United States Patent [19]

Duffett

[11] Patent Number: Plant 6,131

[45] Date of Patent: Mar. 15, 1988

[54] CHRYSANTHEMUM PLANT NAMED THEME

[75] Inventor: William E. Duffett, Salinas, Calif.

[73] Assignee: Yoder Brothers, Inc., Barberton, Ohio

[21] Appl. No.: 833,178

[22] Filed: Feb. 26, 1986

[51] Int. Cl.[4] ..... A01H 5/00

[52] U.S. Cl. ..... Plt./82

[58] Field of Search ..... Plt./82

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Theme particularly characterized by its flat capitulum form; decorative capitulum type; red ray floret color, with excellent color retention under high light conditions; diameter across face of capitulum of up to 10 cm. at maturity; uniform nine week photoperiodic flowering response to short days; medium plant height when grown as a pinched disbudded pot mum; and spreading branching pattern.

3 Drawing Figures

The present invention comprises a new and distinct cultivar of Chrysanthemum, botanically known as *Dentrenthema morifolium*, Ramat., previously *Chrysanthemum morifolium*, Ramat., and referred to by the cultivar name Theme.

Theme, identified as 81889033, was originated from a cross made by me in a controlled breeding program in Salinas, Calif., in 1980. The female parent of Theme was the cultivar identified as 79634005 and by the cultivar name Favor, disclosed in U.S. Plant Pat. No. 5,227. The male parent of Theme, identified as 79632001, was an unnamed seedling.

Theme was discovered and selected as one flowering plant within the progeny of the stated cross by William E. Duffett in October of 1981, in a controlled environment in Salinas, Calif.

The first act of asexual reproduction of Theme was accomplished when vegetative cuttings were taken from the initial selection in January of 1982 in a controlled environment in Salinas, Calif. by a technician working under formulations established and supervised by William E. Duffett.

Horticultural examination of controlled flowerings of successive plantings has shown that the unique combination of characteristics as herein disclosed for Theme are firmly fixed and are retained through successive generations of asexual reproduction.

Theme has not been observed under all possible environmental conditions. The phenotype may vary significantly with variations in environment such as temperature, light intensity and day length.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Theme which, in combination, distinguish this Chrysanthemum as a new and distinct cultivar:

1. Flat capitulum form.
2. Decorative capitulum type.
3. Greyed-red ray floret color, with excellent color retention under high light conditions.
4. Diameter across face of capitulum up to 10 cm. at maturity when grown as a pinched disbudded pot mum.

5. Uniform nine week photoperiodic flowering response to short days.
6. Medium plant height, requiring 0 to 7 long days after pinch prior to short days and one application of 2500 ppm B-9 SP to attain a flowered plant height of 25 to 35 cm. for year around flowerings.
7. Spreading branching pattern.

The accompanying photographic drawings show typical inflorescence and leaf characterstics of Theme, with the colors being as nearly true as possible with illustrations of this type.

Sheet 1 is a color photograph of Theme grown as a pinched disbudded pot mum.

Sheet 2 is a black and white photograph of three views of the inflorescence of Theme.

Sheet 3 is a black and white photograph showing the upper and under sides of the leaves of Theme at three stages of development (mature, intermediate and immature).

Of the commercial cultivars known to the inventor, the most similar in comparison to Theme is Favor, disclosed in U.S. Plant Pat. No. 5,227. Reference is made to attached Chart A, which compares certain characteristics of Theme to the same characteristics of Favor. Similar traits are capitulum form and type, branching pattern, height and flowering response to short days. Theme has a smaller flower than Favor, a darker, more vibrant red flower color, and superior color retention under high light conditions.

In the following description, color references are made to The Royal Horticultural Society Colour Chart. The exact colors for corolla of ray florets are not represented in The Royal Horticultural Society Colour Chart (R.H.S.), and the color values stated below are the closest color values to the actual color of Theme. The color values were determined on plant material grown in Salinas, Calif. on July 18, 1985.

Classification:

*Botanical.*—*Dentrenthema morifolium*, Ramat., cv Theme.

*Commercial.*—Decorative disbud pot mum.

INFLORESCENCE

A. Capitulum:

*Form.*—Flat.

*Type.*—Decorative.

*Diameter across face.*—Up to 10 cm. at maturity.

B. Corolla of ray florets:

*Color (general tonality from a distance of three meters).*—Red.

*Color (upper surface).*—Between 178B and 179A.

*Color (under surface).*—166D.

*Shape.*—Oblong.

C. Corolla of disc florets:

*Color (mature).*—12A.

*Color (immature).*—154B.

D. Reproductive organs:

*Androecium.*—Present disc florets only; scant pollen.

*Gynoecium.*—Present both ray and disc florets.

PLANT

A. General appearance:

*Height.*—Medium; 25 to 35 cm. as a pinched disbudded pot mum with 0 to 7 long days after pinch prior to short days and one application of 2500 ppm B-9 SP.

*Branching pattern.*—Spreading and prolific.

B. Foliage:

*Color (upper surface).*—147A.

*Color (under surface).*—147B.

*Shape.*—Deeply lobed and sharply serrated.

CHART A
COMPARISON OF THEME AND FAVOR

| CULTIVAR | RAY FLORET COLOR | CAPITULUM FORM AND TYPE |
|---|---|---|
| THEME | RED | FLAT DECORATIVE |
| FAVOR | BRONZE RED | FLAT DECORATIVE |

| CULTIVAR | DIAMETER ACROSS FACE OF CAPITULUM | PLANT HEIGHT | FLOWERING RESPONS PERIOD |
|---|---|---|---|
| THEME | UP TO 10 CM. | MEDIUM | NINE WEEK |
| FAVOR | 80 to 120 mm. | MEDIUM | NINE WEEK |

COMPARISONS MADE OF PLANTS GROWN AS PINCHED AND DISBUDDED POT MUMS IN SALINAS, CALIFORNIA

I claim:

1. A new and distinct Chrysanthemum plant named Theme, as described and illustrated, and particularly characterized as to uniqueness by the combined characteristics of flat capitulum form; decorative capitulum type; red ray floret color, with excellent color retention under high light conditions; diameter across face of capitulum of up to 10 cm. at maturity; uniform nine week photoperiodic flowering response to short days; medium plant height when grown as a pinched disbudded pot mum; and spreading branching pattern.

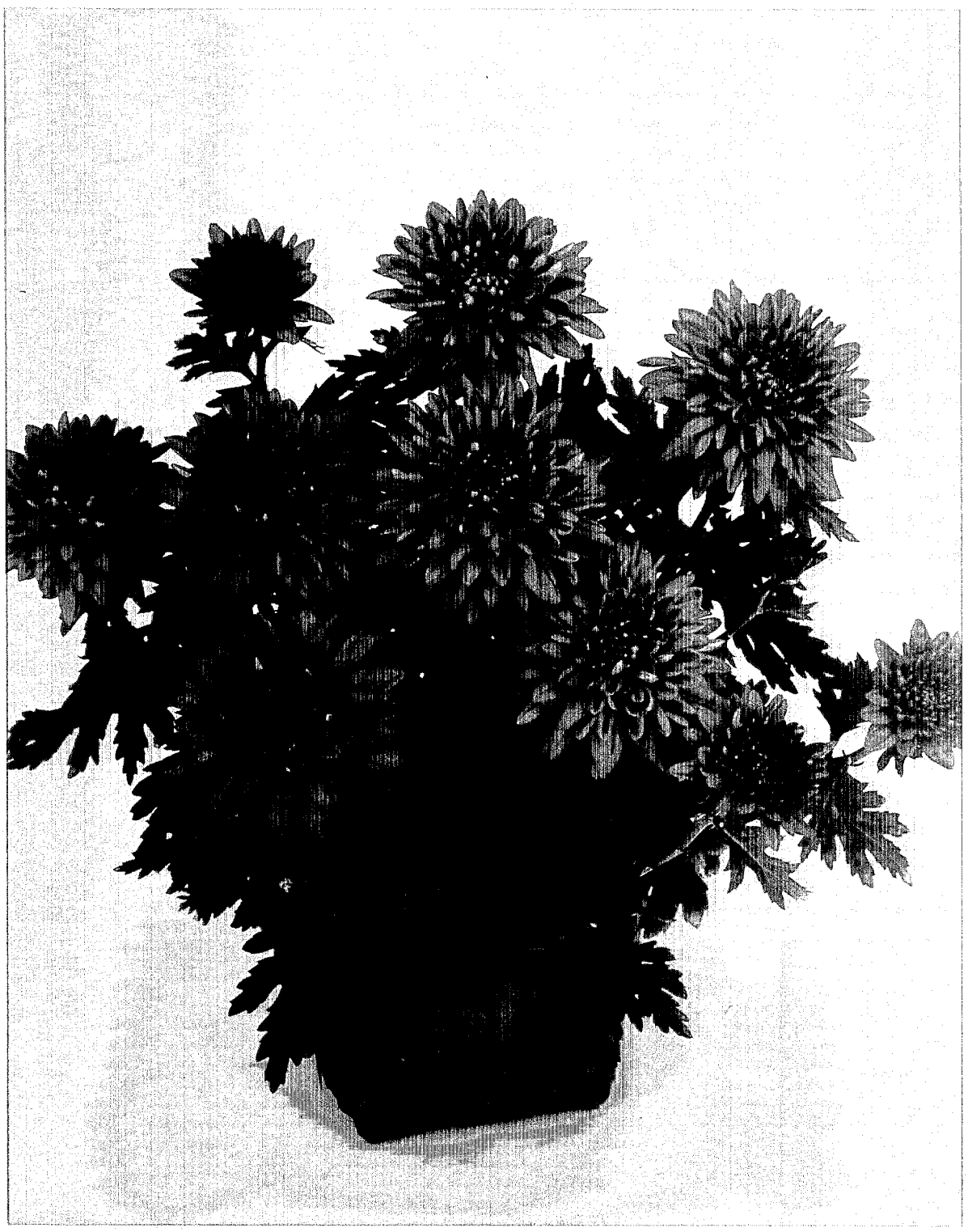

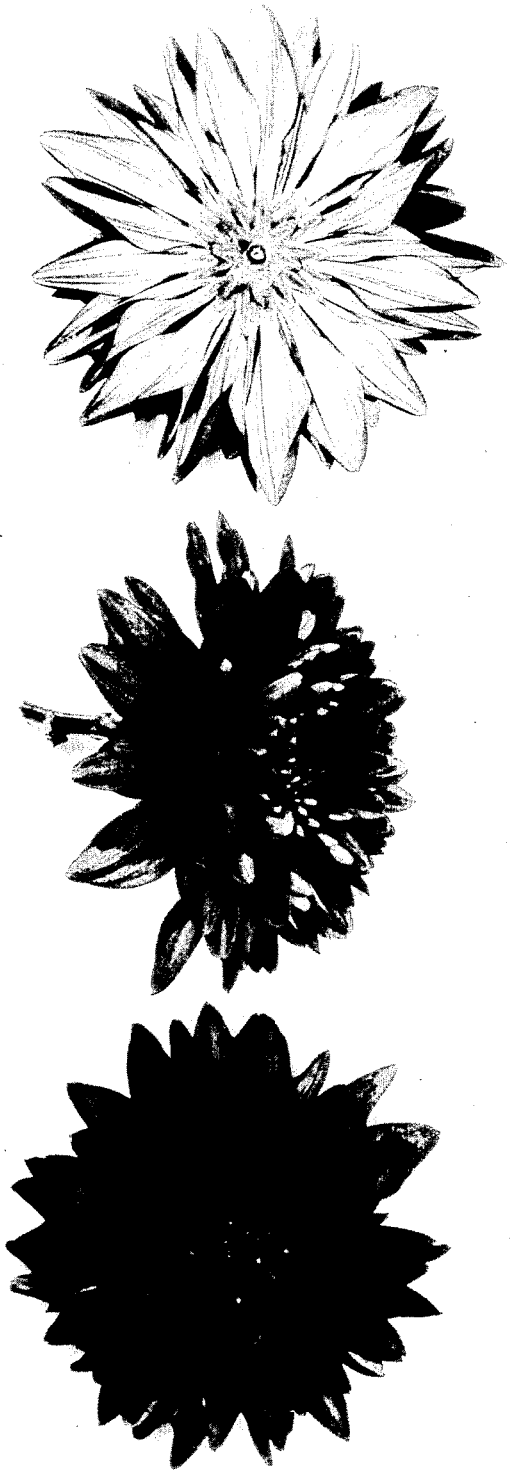

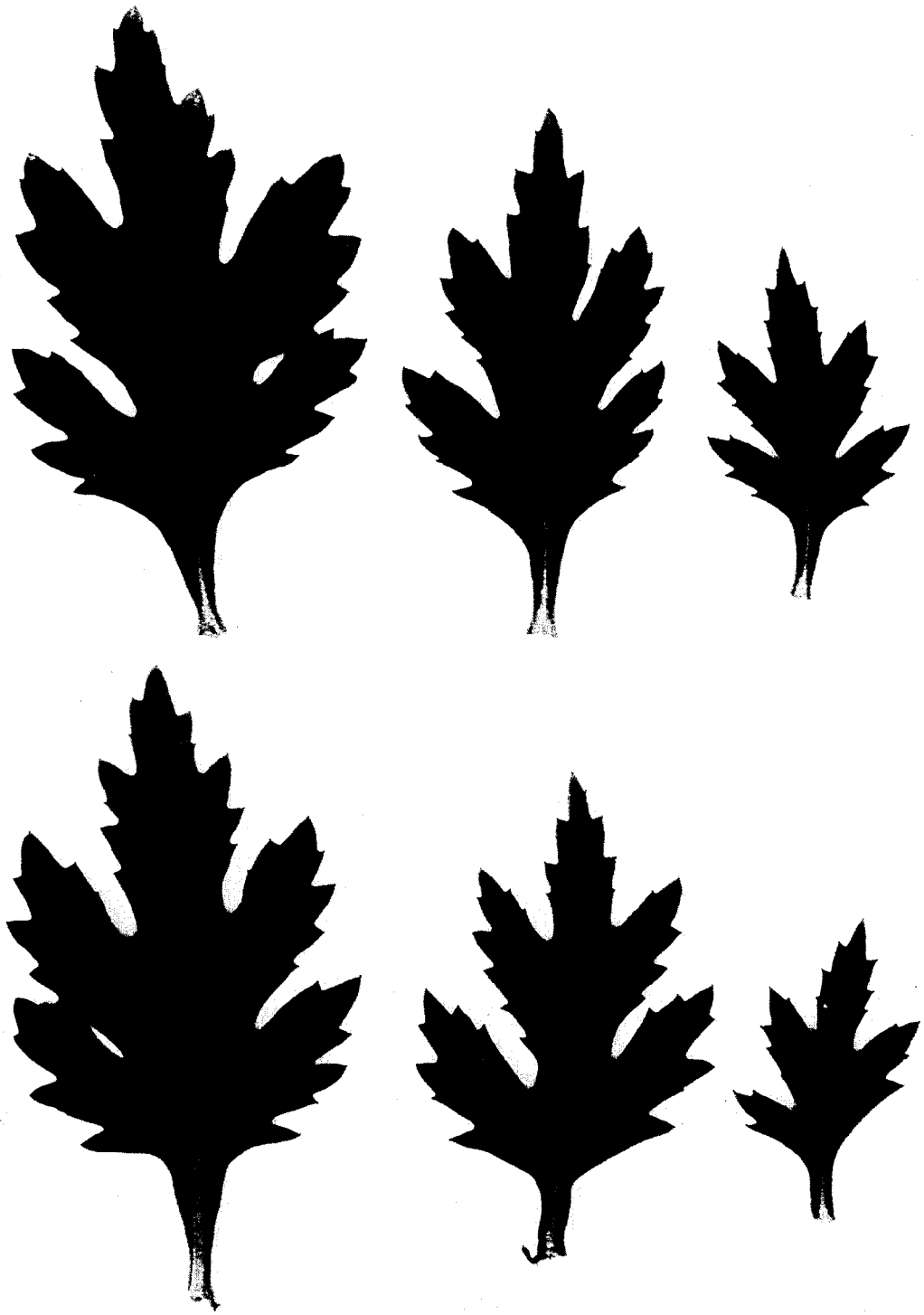

* * * * *